United States Patent
Heidel

(10) Patent No.: US 7,726,593 B2
(45) Date of Patent: Jun. 1, 2010

(54) DEVICE FOR THE IN-SITU DISPOSAL OF SANITARY WASTE, IN PARTICULAR OF INCONTINENCE ARTICLES AND METHOD FOR THIS

(75) Inventor: Werner Heidel, Viersen (DE)

(73) Assignee: Teeuwen Präzisions GmbH, Viersen (DE)

( * ) Notice: Subject to any disclaimer, the term of this patent is extended or adjusted under 35 U.S.C. 154(b) by 565 days.

(21) Appl. No.: 11/292,915

(22) Filed: Dec. 1, 2005

(65) Prior Publication Data
US 2006/0118665 A1 Jun. 8, 2006

(30) Foreign Application Priority Data

| Dec. 2, 2004 | (DE) | 20 2004 018 714 U |
| Jan. 6, 2005 | (DE) | 20 2005 000 148 U |
| Jan. 31, 2005 | (DE) | 20 2005 001 569 U |

(51) Int. Cl.
*B02C 1/00* (2006.01)
*B02C 23/02* (2006.01)
(52) U.S. Cl. .................. 241/21; 241/29; 241/186.5
(58) Field of Classification Search .............. 241/21, 241/29, 24.11, 152.2, 278.1, 186.5
See application file for complete search history.

(56) References Cited

U.S. PATENT DOCUMENTS

| 5,232,584 A | 8/1993 | Wang et al. | |
| 2003/0019961 A1* | 1/2003 | Hohnen et al. | 241/23 |

FOREIGN PATENT DOCUMENTS

| DE | 691 24 107 | 6/1997 |
| DE | 198 53 520 | 5/2000 |
| WO | 03/009942 | 2/2003 |

* cited by examiner

*Primary Examiner*—Faye Francis
(74) *Attorney, Agent, or Firm*—Friedrich Kueffner

(57) ABSTRACT

The device for the disposal of sanitary waste consists of a fixed drum-type container (20) with a horizontal central axis (MA) and with inlet pipes for dosed wash liquid (WF), for sanitary liquid (HF) and for dosed chemicals (CH), whereby a discharge duct (65) for the carrying-off of the comminuted sanitary waste interspersed with wash liquid from the bottom area of the container (20) is provided in the bottom area of the container (20), in the inner space (27) of which a knife disk (30) which can be rotatably driven is placed in the area of one of its both vertical front walls (21; 22) with shearing knives (31) turned to the inner space (27) of the container (20), whereby an ascendingly guided compressor screw (60) follows the conveyor screw (65), compressor screw which forms with a shear sieve sheet (70) a functional unit for separating the comminuted sanitary waste containing solid components from the wash liquid (WF) with the constituents of the sanitary waste which are dissolved therein and the wash liquid is supplied to a drain (85) over a discharge duct (80), whereby the rest of the comminuted sanitary waste freed from the liquid and containing solid constituents is fed in the upper area (61*b*) of the housing (61) to a collecting container (95).

9 Claims, 9 Drawing Sheets

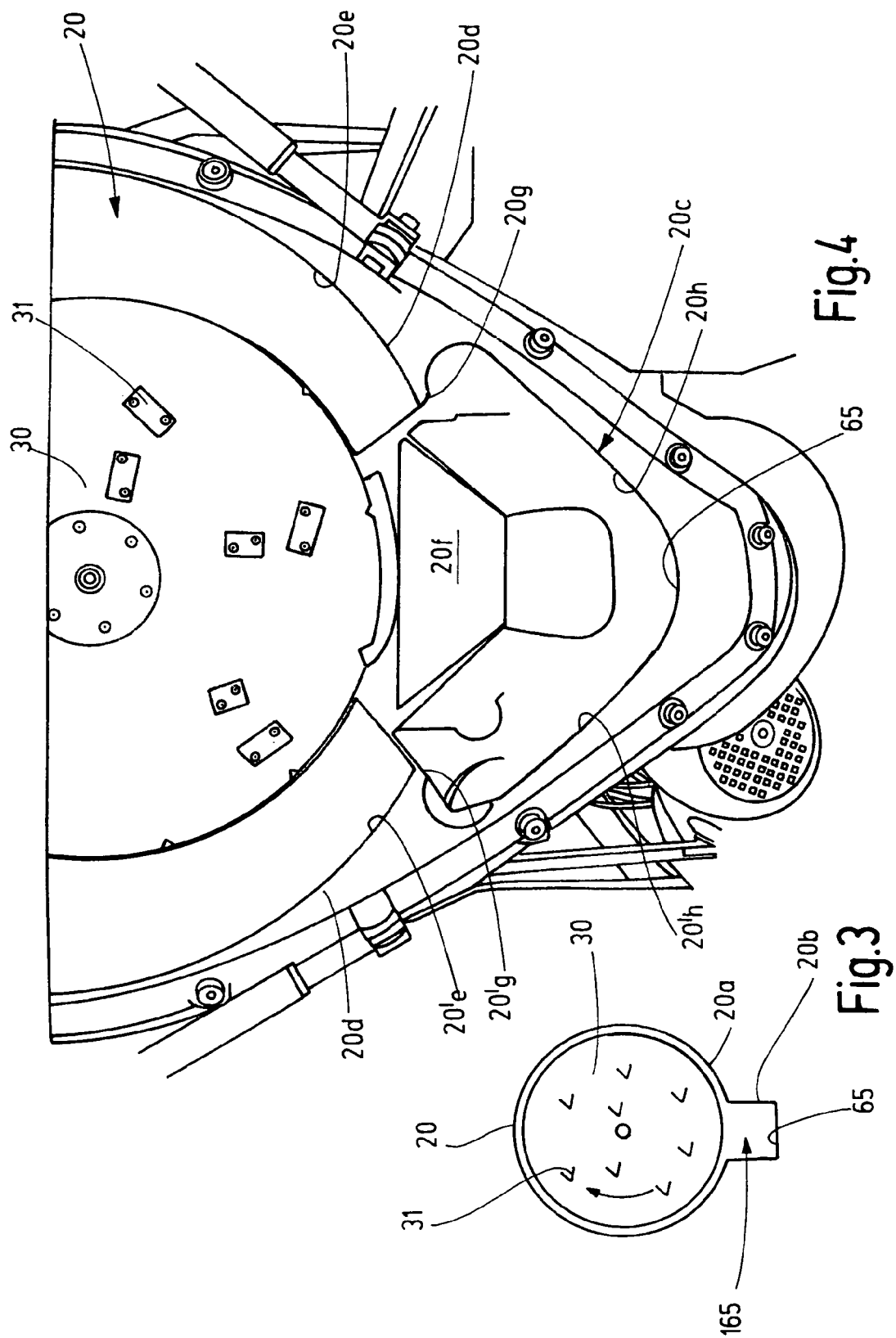

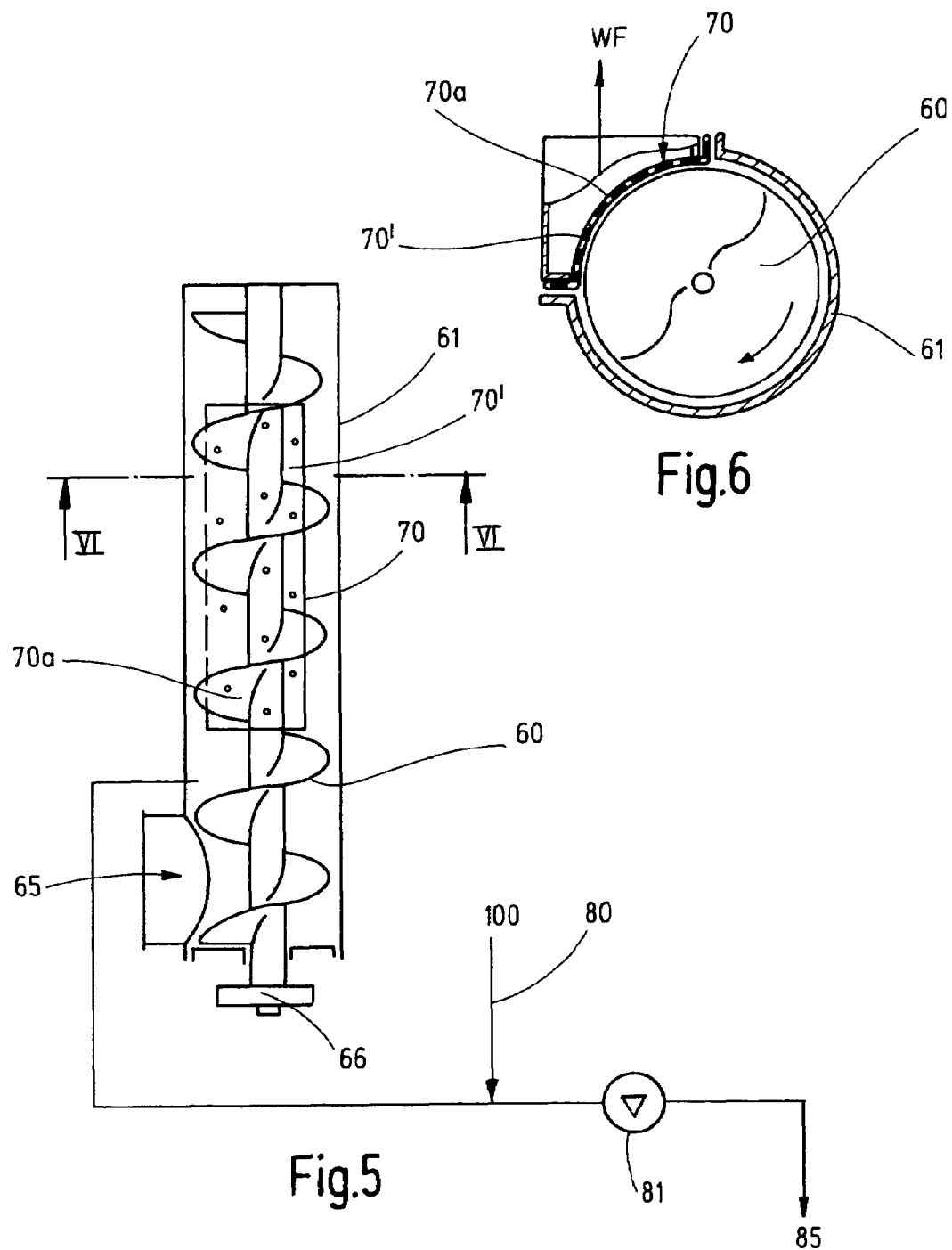

DEVICE FOR THE IN-SITU DISPOSAL OF SANITARY WASTE, IN PARTICULAR OF INCONTINENCE ARTICLES AND METHOD FOR THIS

FIELD OF APPLICATION

The invention relates to a device for the in-situ disposal of sanitary waste, in particular of incontinence articles, as well as to a method for this.

PRIOR ART

Through the DE-A-691 24 107, we know a method for the treatment of absorbent sanitary paper products for separating such products into their components or into components thereof which have a shape which is appropriate for recycling or for reutilization, whereby the products comprise at least synthetic, cellulose and superabsorbent polymer ("SAP") solid fractions, the method comprising the following steps: treatment of the products in disintegrated form in an aqueous solution bath in order to solve soluble material and to treat the SAP so that its sources are inhibited, prevented or reversed in aqueous media and separation of the solution of soluble material from at least one of the solid fractions.

The device used for carrying out this method comprises a rotatable tiltable cylindrical drum with a first and with a second end which can contain and/or receive an aqueous solution and which is tiltable from a horizontal position into a tilted position, tilted position in which the second end is lower than the first end, whereby the first end is configured for loading the product into the inner part of the drum and for containing the product therein, whereby the second end possesses an outlet for delivering the product out of the drum, besides means for rotating the drum in at least one of horizontal and tilted positions, means for tilting the drum from the horizontal position into the tilted position, whereby for the treatment of absorbent sanitary paper products in order to separate such products into their components or into components thereof, the form of which is appropriate for recycling or for reutilization, by using means for the separation of solids from liquids in the drum, there is a stirrer in the inside of the drum in order to cause a communication of the product in the drum. This method and the e device configured for this should achieve that absorbent sanitary paper products with superabsorbent polymers can be treated in such a way that a few components or all components of such products can be recovered in a form which facilitates the recycling or another use of these components. A disposal is not provided for.

Moreover, a method and a device for the disposal of sanitary waste is known from the DE-A-198 53 520. In order to reduce the volume and the weight of sanitary waste and to stop the nuisance through bad smells, the sanitary waste is first mechanically disintegrated before it is brought into contact with a sanitary liquid which contains water with a sanitary additive usable in transportable toilets in such a quantity that the cellulose contained in the sanitary waste with gel grains is dissolved together with the body excrements contained therein. The used sanitary liquid is evacuated into the sewer, the remaining rest of the comminuted sanitary waste substantially made of synthetic material being recycled after dewatering. However, the sanitary additives used for this method do not allow any treatment of the superabsorbent substances contained among others in the sanitary waste such as the polymers.

It is known that absorbent sanitary paper products are made of a nonwoven made of a liquid permeable material, for example of a liquid permeable membrane made of an appropriate synthetic material or of woven products made of cotton, of a rear layer impermeable to liquid, degradable plastic foils on starch base, woven fabric or rubber and an absorbent or adsorbent core of airlaid cellulose fluffs and/or of synthetic cellulose containing bound or unbound polypropylene filaments, hemp or of other adsorbent fiber materials. The core is enclosed or wrapped in a crepe envelope made of wet-strength paper layers or of a material with similar properties. The wrapping of the core can be naturally breathing, biodegradable, odour inhibiting or degradable or soluble in another manner. The core can also be made of a material made of superabsorbent polymer (SAP) material according to DE-A-691 24 107. Sanitary napkins and incontinence products use pressure sensitive adhesives for reclosable adhesive tape brackets or similar closing mechanisms. These incontinence products can also be provided with pressure sensitive adhesives for adhesive lines in order to be able to fix a fixture, for example in form of a lining, on the underwear of the female or the male wearing person. The use of absorbent sanitary paper products is, in fact, practical or necessary as well; however, the disposal thereof causes many problems. According to the known methods and by means of the known devices, such absorbent sanitary paper products can be treated in such a manner that a few components of such products or all components thereof can be recovered in a form which facilitates recycling or another use of these components.

Furthermore, from the WO 03/009942 we know a device for the in-situ disposal of incontinence articles. This device comprises a basic housing in which a device is placed which is made of a drum-type housing with an upper filling opening and a cylindrical drum placed in the inner space of the casing, fixed or being able to be put in rotation about a horizontal axis of rotation and with two wall plates closing both drum openings on the front side, the first wall plate of which being connected with the drum housing and the second wall plate being displaceable in the longitudinal direction of the axis of rotation of the drum and being configured rotatable about its central axis, whereby both front-sided drum wall plates carry on their opposed wall faces comminuting knives penetrating in the drum inner space. Furthermore, inlets for wash water, for a sanitary liquid and for chemicals as well as outlets for the solid constituents of the waste which have been sucked off are provided for.

Aim, Solution, Advantage

Thus, the aim of this invention is to create a compact device of the above described type which takes a minimal space which is very economical and which has a low susceptance to trouble with which incontinence articles can be decomposed into the individual components by using a high cutting, tearing and breaking-up effect in order to recycle in-situ the obtained disintegrated solid components of the material to dispose of and thus to economically dispose of the whole product or to bring it to a central industrial processing installation, whereby a reduction of the forces to be applied for the disintegration and for the separation of the material to dispose of should be obtained. Moreover, the device should comprise only a few components so that the device can be produced economically. Due to the fact that all components are lodged in a housing in the smallest space, the use is also economically possible for example in homes with a low number of occupants.

According to the invention, the device for the disposal of sanitary waste consists of a housing in which a fixed drum-type container with a horizontal central axis and with a filling opening for the sanitary waste as well as with an inlet pipe for dosed wash liquid, an inlet pipe for a dosed sanitary liquid for preventing odors and for disinfection and an inlet pipe for dosed chemicals in powdered or liquid state for conditioning the superabsorbers such as solid products made of plastics or superabsorbent polymer products or gel bodies such as polymers in the sanitary waste and in particular in the sanitary napkins contained in the sanitary waste, whereby a discharge device which is integrated into the container body is provided in the bottom area of the container, preferably a screw conveyor duct for the conveying-off of the comminuted sanitary waste interspersed with the wash liquid out of the bottom area of the container, in the inner space of which a vertical knife disk which can be driven into rotation is placed in the area of one of its both side walls with tearing knives turned to the inner space of the container for tearing and disintegrating the sanitary waste and a compressor screw following the screw conveyor and placed in an approximately tubular housing with a different gradient and a different web thickness, whereby the screw conveyor is guided into the bottom-sided area of the compressor screw which forms a functional unit with a shear sieve sheet placed in the inner space of the housing and extending in the longitudinal direction of the compressor screw for separating the comminuted sanitary waste containing solid components from the wash liquid with the constituents of the sanitary waste dissolved therein in such a manner that the compressor screw and the shear sieve sheet cooperate in the manner of scissors in order to avoid a plugging of the shear sieve sheet, whereby the wash liquid with the constituents of the sanitary waste which are dissolved therein is fed to a discharge duct over a discharge pipe by means of a pump and whereby the rest of the comminuted sanitary waste freed from liquid and containing solid constituents is fed in the upper area of the housing with the compressor screw to a collecting receiver, are placed, whereby the control of the admission for the wash liquid and the dosing pumps for the sanitary liquid and for the chemical, the control for the driving device for the knife disk and the controls for the discharge device, the compressor screw and the pumps are combined in a program switching device or are carried out by means of a free programmable device.

With the device according to the invention, it is possible to economically dispose in-situ of sanitary waste and in particular of incontinence articles with the possibility to let off, as far as allowed, the single obtained components or, eventually, to pelletize them. The comminution of the material to dispose of is carried out by means of the knife disk without a high expenditure of forces or energy being necessary for this. The wash liquid with the constituents of the material to dispose of dissolved therein and the comminuted solid components of the material to dispose of are passed over from the inner space of the drum-type container into a compressor screw and drawn off by means of a water pump optimized to vacuum, whereby the wash liquid with the constituents of the material to dispose of dissolved therein is then separated by means of the compressor screw in relation with a specially created shear sieve sheet from the comminuted solid components of the material to dispose of. The wash liquid is then fed to the discharge duct, whereas the comminuted solid components of the material to dispose of are supplied to a collecting receiver, whereby it is also possible to pelletize the solid components by means of an appropriate device.

A further advantage consists in the in-situ disposal of the conditioned sanitary waste or of the incontinence articles, whereby a wardwise disposal is also possible, for example in old people's homes, hospitals and children's homes. A pelletizing of the residual valuable substances, such as plastics and cellulose, is also possible. Single quantities as well as bigger quantities of incontinence articles can be disposed of. The whole process can be carried out at low temperatures. Cold water is preferably used as wash liquid. The feeding of the device can be carried out manually or also mechanically and automatically, for example by means of conveying belts. It is advantageous that an in-situ disposal is possible without storage and without intermediate transports.

The device has only a few components so that the susceptance to failure of the device is considerably reduced. It has shown that a good separation of the wash liquid with the constituents of the material to dispose of which are dissolved therein from the comminuted solid components of the material to dispose of is achieved by means of the compressor screw used in connection with the shear sieve sheet so that an additional posterior treatment to avoid eventually still contained residual liquid in the comminuted material to dispose of is not necessary.

So, the configuration of the discharge device is particularly advantageous if this device is configured as a conveyor screw. The conveyor screw guarantees a safe and quick transport of the material which has to be discharged from the container inner space.

In order to remove eventually remaining residual liquid in the comminuted material to dispose of, a further embodiment provides that a compressor nozzle with an upwards tapered section for separating the residual liquid is configured in the upper area of the housing with the compressor screw of the device, section which is connected with the compressor screw by a connecting line with the discharge for the liquid from the housing.

The shearing knives of the knife disk are formed in such a way that sanitary waste or the incontinence articles are not only cut up but in particular torn open and chopped during a rotation of the knife disk in working direction. Furthermore, the shape, the configuration and the arrangement of the shearing knives is chosen such that favourable flow conditions are adjusted when the device is working.

Moreover, the invention provides a method for carrrying out an in-situ disposal of sanitary waste by using the device according to the invention which consists in that a.) the sanitary waste is conditioned, torn into pieces and comminuted in a drum-type container by simultaneously supplying wash water, preferably cold wash water, chemicals, sanitary liquid and disinfectants by means of shearing knives of a rotatably driven knife disk, then b.) the comminuted product is supplied to a compressor screw for separating the comminuted sanitary waste containing solid components from the wash liquid by means of a shear sieve sheet by simultaneously cooperating in the manner of scissors of the compressor screw with the shear sieve sheet for avoiding a plugging of the shear sieve sheet and then c). the wash liquid is supplied with the soluble constituents of the sanitary waste dissolved in the wash liquid to a discharge duct and the rest of the comminuted sanitary waste containing solid constituents and freed from the wash liquid is supplied to a collecting receiver.

Furthermore, it is provided for that chemicals are supplied for the conditioning process of the sanitary waste in the container for the conditioning of the superabsorbers such as solid products made of plastics or superabsorbing polymer products or gel bodies, preferably calcium chloride.

SHORT DESCRIPTION OF THE DRAWINGS

The object of the invention is represented as an example in the drawings.

FIG. 3 shows a vertical section through a drum-type container.

FIG. 4 shows a vertical section through the drum-type container of the embodiment according to FIG. 1.

FIG. 5 shows schematically the housing with the compressor screw and the shear sieve sheet.

FIG. 6 shows a vertical section through the housing with the compressor screw and the shear sieve sheet according to the line VI-VI in FIG. 5.

DETAILED DESCRIPTION OF THE INVENTION AND BEST WAY OF CARRYING OUT THE INVENTION

Figure 1:
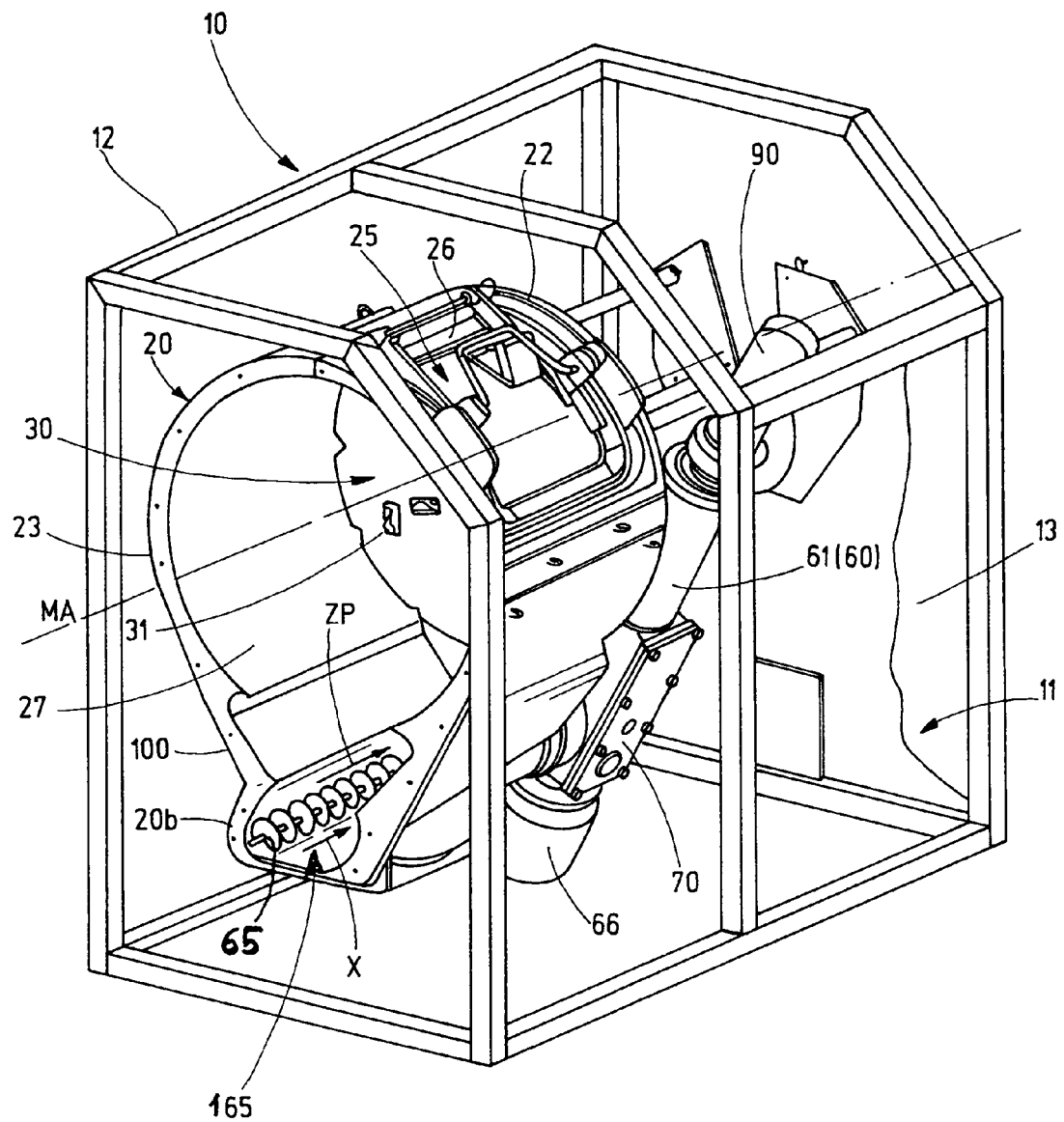
FIG. 1 shows a graphic view of the disposal device, with the mechanical comminution of the sanitary waste, the wall plates being removed.
Figure 2:
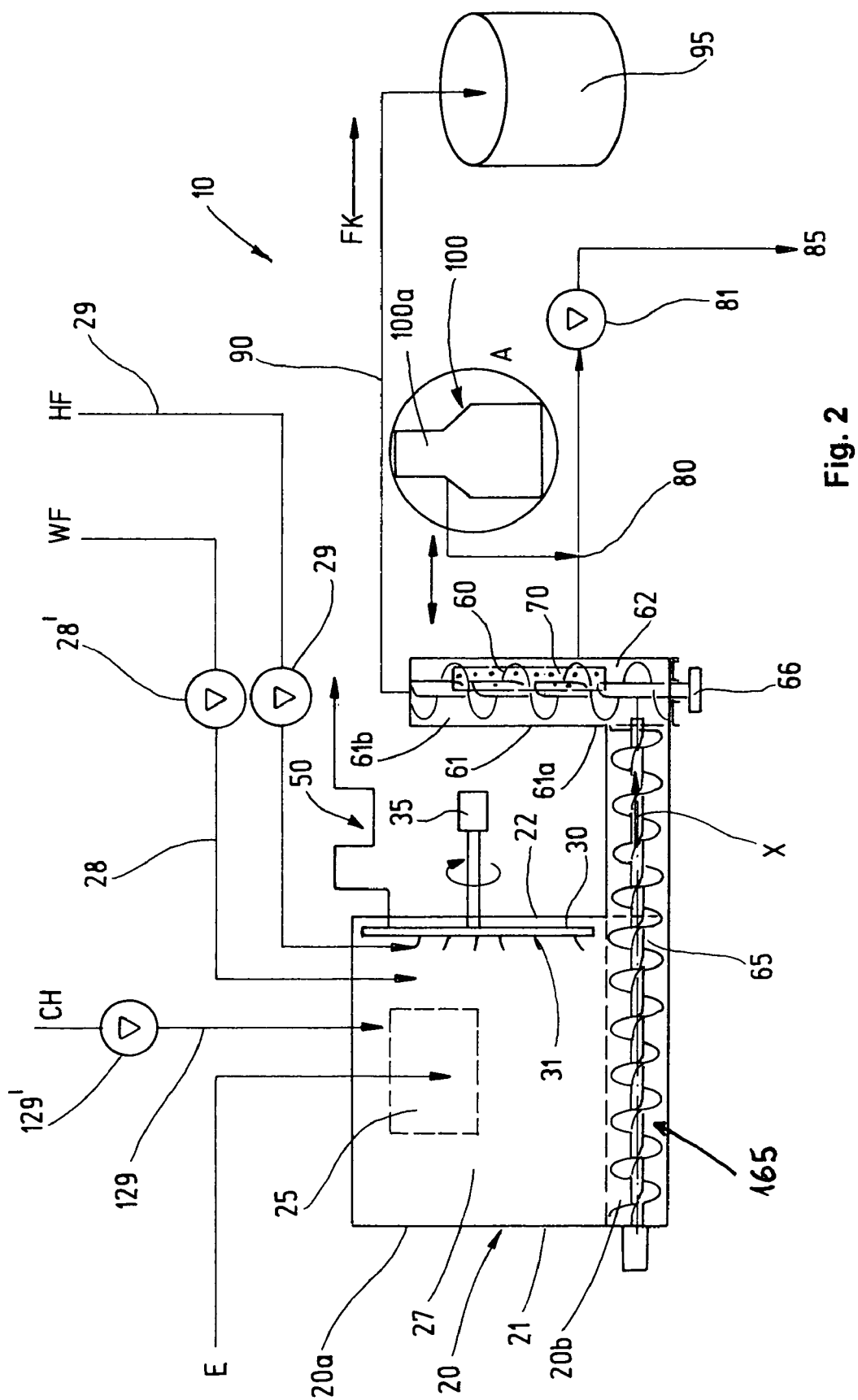
FIG. 2 shows schematically the structure of the disposal device with its various components such as the drum-type container with knife disk, discharge device and compressor screw with shear sieve sheet.

According to FIGS. 1 and 2, the device 10 for the disposal of sanitary waste, in particular of incontinence articles, designated hereunder as material to dispose of E, consists of a housing 11 which is made of a frame 12 with side walls 13.

A drum-type fixed container 20 with a horizontal central axis MA and with vertical front walls 21, 22 is placed in the frame 12. Preferably, the container 20 is positioned elastically in the frame 12. The container 20 has in its upper area a filling opening 25 which can be closed by means of a cover 26 for the material to dispose of E.

In the inner space 27 of the container 20, a vertical knife disk 30 with shearing knives 31 which can be driven rotating by means of a driving device 35 is placed in the area of one of its both front walls 21, 22, whereby the rotation of the knife disk 30 can take place constantly in the one direction or in the other direction, whereby preferably a continuous change of the direction of rotation can take place so that the shearing knives 31 provided on the knife disk 30 can be fully effective and thus the tearing and comminuting process of the material to dispose of improved.

Wash liquid WF, preferably cold wash water, sanitary liquid HF for preventing odors and for disinfection and chemicals CH are fed in powder or liquid state to the inner space 27 of the container 20 by feeding pipes 28, 29, 129 with integrated dosing pumps or devices 28', 29', 129', whereby the chemical is used to condition the superabsorbers such as polymers which are contained in the sanitary waste and in particular in the sanitary napkins contained in the sanitary waste. In particular calcium chlorides or other appropriate chemicals, even in combination with other chemicals, can be used as chemicals. Such chemicals which can be easily disposed of are essentially used. Oxygen, ozone, chlorine or compounds of chlorine can be used as disinfectants.

For the conditioning process of the sanitary waste, chemicals are supplied to the container 20 for the conditioning of the superabsorbers such as solid products made of plastics or superabsorbing polymer products or gel bodies, preferably calcium chloride.

The drum-type container 20 made of steel, plastics or other appropriate materials has in its bottom area 40 a discharge device 165 placed in longitudinal direction of the container which is configured as a conveyor screw 65. The comminuted product ZP which has been accumulating on the bottom in the inner space 27 of the container 20 is conveyed-off by the conveyor screw 65. This comminuted product ZP consists of wash liquid with constituents of the material to dispose of E dissolved therein and of the comminuted solid component FK of the material to dispose of E. The discharge device 165 can also configured in another way, for example as a conveying band or as a hydraulically actuated slide. The comminuted product ZP is supplied by this discharge device 165 from the inner space 27 of the container 20 to a compressor screw 60 in direction of the arrow X with the aid of a suction pump or of a water pump constituting a vacuum.

The tubular housing 61 which receives the compressor screw 60 is placed laterally to the drum-type container 20. The housing 61 with the compressor screw 60 is guided vertically or ascending (FIGS. 1 and 2).

The drum-type container 20 is made of an upper cylindrical container body 20a which changes on the bottom side into a tapering section 20b which forms the conveyor screw 65 (FIG. 3). Due to this configuration of the container 20, a swirl of the comminuted product is achieved during the operation of the device to which the shape of the shearing knives 31 of the knife disk 30 contributes.

FIG. 4 shows an embodiment for which the drum-type and cylindrical container 20 turns on the bottom side into a conically tapering section 20c, in the bottom-sided closing of which the conveyor screw 65 is placed. The drum wall 20d which turns into the section 20c delimits with its end sections 20e, 20'e an opening 20f, the size of which is smaller than the drum diameter. The section 20c with the conveyor screw 65 follows this opening 20e. The container wall sections 20e, 20'2 turn into tongue-shaped sections 20g, 20'g which are followed by the conical wall faces 20f, 20'h of the container section 20c so that the cross section form of the container 20 which is represented in FIG. 4 is obtained.

In the lower area 61a of the housing 61 of the compressor screw 60, the housing inner space 62 is connected by the conveyor screw 65 with the inner space 27 of the container 20 so that the conveyor screw 65 is guided into the receiving area of the compressor screw 60. The drive for the conveyor screw 65 is not represented on the drawings. iIn this way, the comminuted product ZP can be directly supplied from the container 20 to the compressor screw 60. The drive for the compressor screw 60 is represented by 66 in FIGS. 1 and 2. An embodiment for which the compressor screw has different gradients and a different web thickness is used as compressor screw 60. The comminuted product ZP is conveyed by means of the compressor screw into the upper area 61b of the housing 61. The separation of the wash liquid with the constituents of the material to dispose of E dissolved therein from the comminuted solid component FK of the material to dispose of takes place by means of a shear sieve sheet 70 provided in the housing 61. The compressor screw 60 which follows the conveyor screw 65 is placed in a tubular housing 61. The conveyor screw 65 is guided into the bottom-sided area of the compressor screw 60 which forms a functional unit with the shear sieve sheet 70 placed in the inner space 62 of the housing 61 and which extends in the longitudinal direction of the compressor screw for separating the comminuted sanitary waste containing comminuted solid components from the wash liquid WF with the constituents of the sanitary waste dissolved therein in such a manner that the compressor screw 60 and the shear sieve sheet 70 cooperate in the manner of scissors in order to avoid a plugging of the shear sieve sheet 70, whereby the wash liquid WF with the constituents of the sanitary waste which are dissolved therein is sucked by a discharge pipe 80 by means of a pump 81 and fed to a discharge duct 85 (FIGS. 2, 5, 6 and 7). The rest FK of the comminuted sanitary waste freed from the liquid and containing solid constituents is fed to a collecting receiver 95 in the upper area 61b of the housing 61 with the compressor screw 60.

The accumulating wash liquid WF with the constituents of the material to dispose of which are dissolved therein is sucked off by a discharge pipe 80 with an integrated pump 81 and is supplied to the discharge duct 85.

An additional removal of residual liquid from the comminuted product ZP can be achieved by a special configuration of the transition area from the inner space 62 of the housing 61 to the discharge 80. This configuration consists in a compressor nozzle 100 with an upper tapering section 100a which is represented in FIG. 2 by A.

Figure 7:
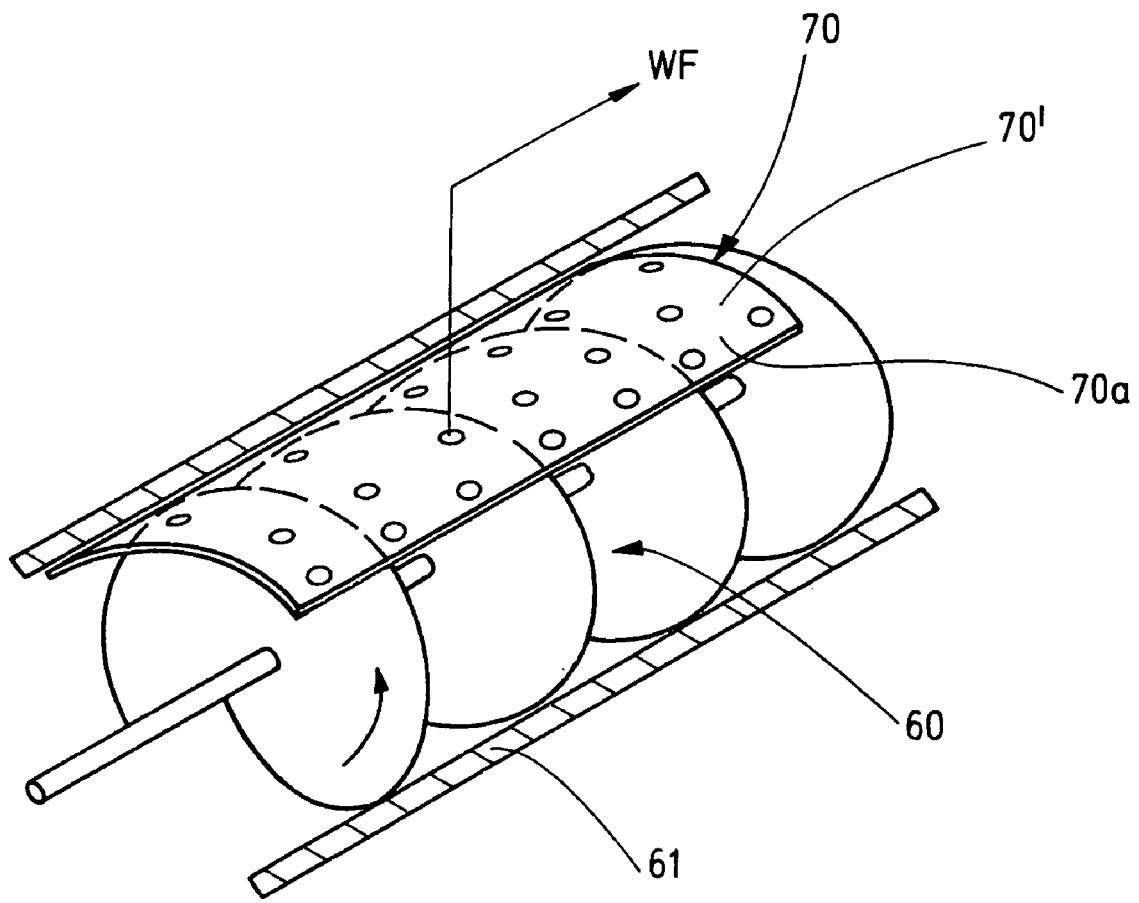
FIG. 7 shows a graphical partial view of the housing with the compressor screw and the shear sieve sheet.

The shear sieve sheet 70 is configured as an insert body 77 which can be placed in the housing 61 of the compressor screw 60, whereby the curved sieve surface 70a is placed lying without any distance to the rotation surface of the compressor screw 60 so that the compressor screw 60 shears along the inner wall surface of the shear sieve sheet 70 (FIGS. 5, 6 and 7).

Figure 8:
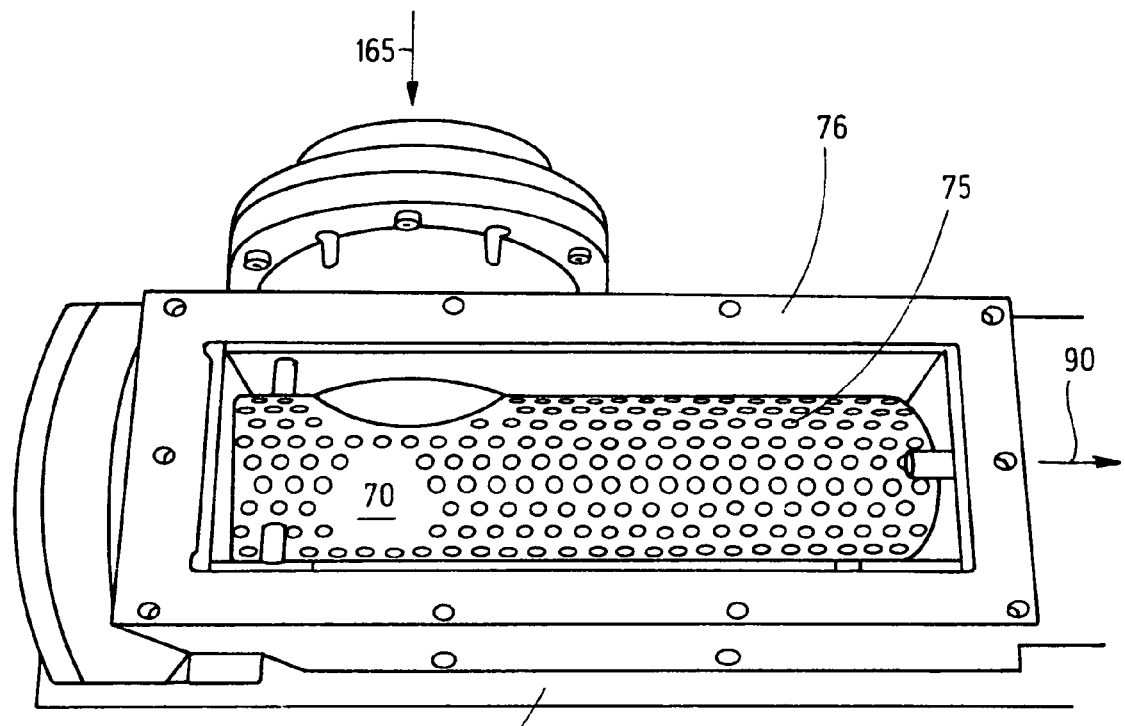
FIG. 8 shows the box-type opening of the housing of the compressor screw in the area of the shear sieve sheet.
Figure 9:
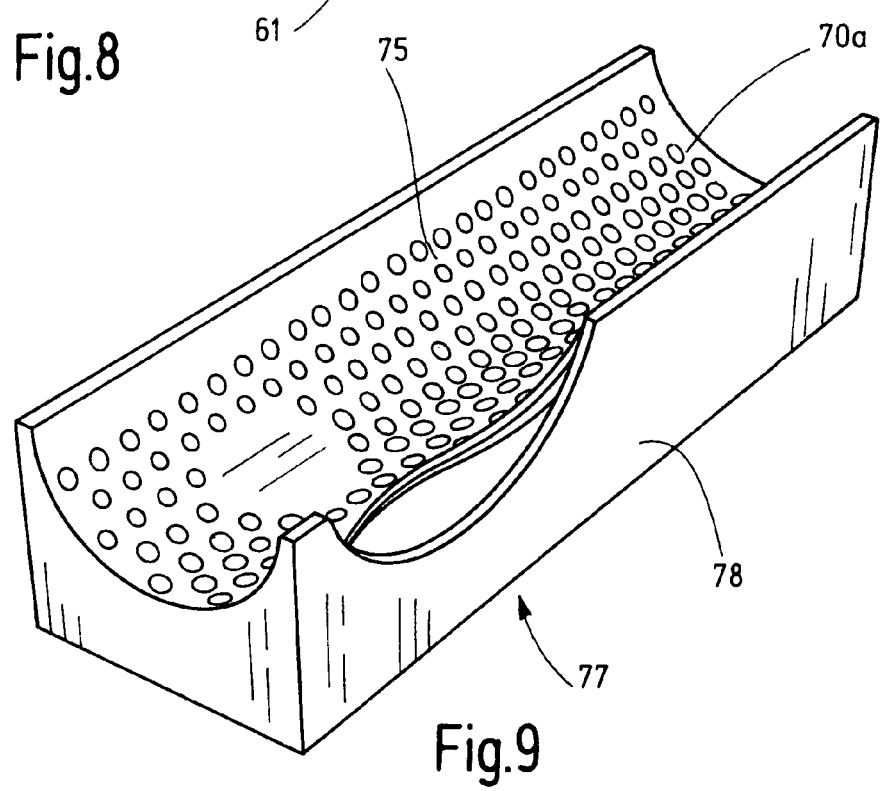
FIG. 9 shows a graphical view of the housing with the shear sieve sheet.
Figure 10:
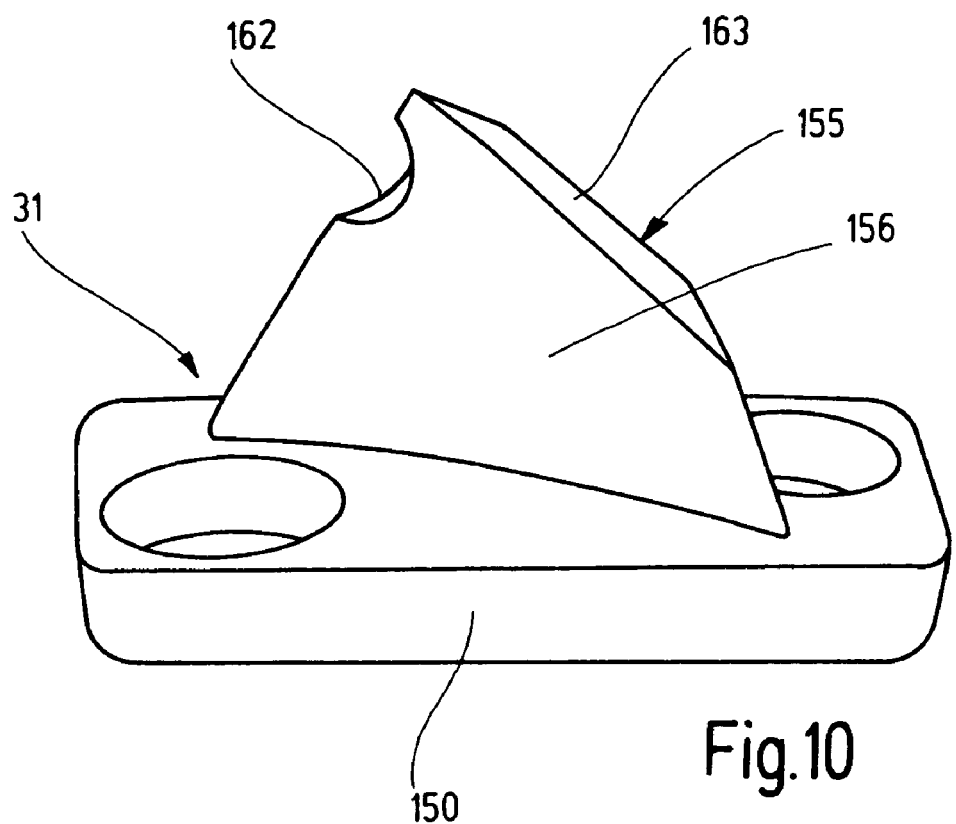
FIG. 10 shows a graphical side view of a shearing knife for the mechanical comminution of the sanitary waste.

The shear sieve sheet 70 is placed, as represented in FIG. 8, in the area of an opening 75 which can be closed and which is formed in the housing 61 which receives the compressor screw 60 in a box-shaped housing muff 76 which is connected with the housing 61. The insert body 77 formed as a shear sieve sheet 70 is placed in this box-shaped housing muff 76 and consists of a box-shaped frame 78 in which the curved sieve surface 70a is placed (FIG. 9). The insert body 77 is placed interchangeable in the housing 61.

The knife disk 30 carries on its wall surface turned to the inner space 27 of the container 20 a certain number of shearing knives 31 for comminuting, breaking up and tearing the material to dispose of. This being, the matter can be of individually placed shearing knives 31. However, ring-shaped placed shearing knives can be used as well, whereby several shearing knive rings inserted the one in the other can be used with a diameter reducing towards the center.

In order to achieve an effective comminution, dividing and tearing of the material to dispose of in connection with the wash liquid, it is advantageous that the length of the container 20 corresponds approximately to the diameter of the front walls 21 or 22 of the container 20, whereby the one of the two front walls 21, 22 is not represented in FIG. 1. The diameter of the knife disk 30 should correspond approximately to the diameter of the front walls 21, 22 in the area above the conveyor screw 65 of the container 20. The container 20 is placed fixed in the frame 12 of the housing 11 of the device 10 and has approximately a cylindrical shape.

In order to guarantee a perfect transfer of the material to dispose of which is conditioned in the container 20 into the conveyor screw 65, the container side wall 23 turns into a preferably conically downwards tapering section 20b which turns into the conveyor screw 65 (FIGS. 1, 2, 3 and 4). The conveyor screw 65 is parallel to the central longitudinal axis of the container 20.

For an effective comminution of the sanitary waste, each shearing knife 31 has an optimized knife grinding. According to the embodiment according to FIG. 10 to 15, each shearing knife 31 is made of an approximately rectangular fixing plate 150 and of a plate-shaped and approximately triangular knife body 155 placed standing perpendiculary on the fixing plate 150 and diagonally to this. The fixing plate 150 is provided with openings for receiving fixing screws in order to be able to fix the shearing knife 31 on the knife disk 30. However, other fixing types can also be used. The fixing plate 150 can also have another geometrical shape configuration. However the rectangular configuration is advantageous since due to the placement of the knife body 155 in diagonal direction to the rectangular fixing plate 150 the knife body 155 can have a length which corresponds approximately to the diagonal of the fixing plate 150.

The knife body 155 is configured plate-shaped; it is fixed standing perpendicularly on the fixing plate 150 and has an approximately triangular configuration, whereby the knife body rests upright with its triangular base on the fixing plate 150.

Figure 11:
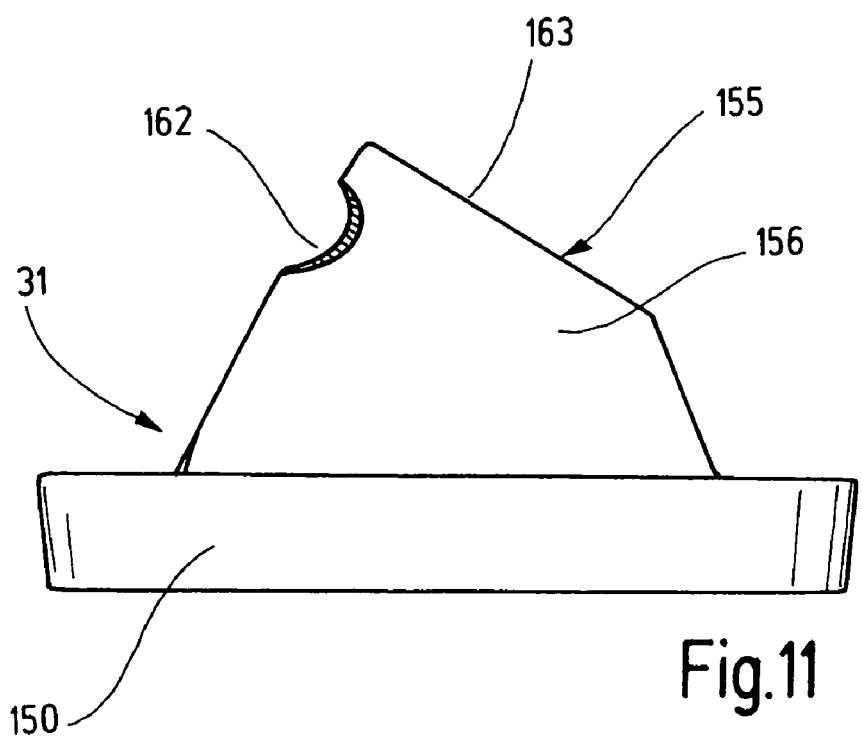
FIG. 11 shows a side view of the shearing knife.
Figure 12:
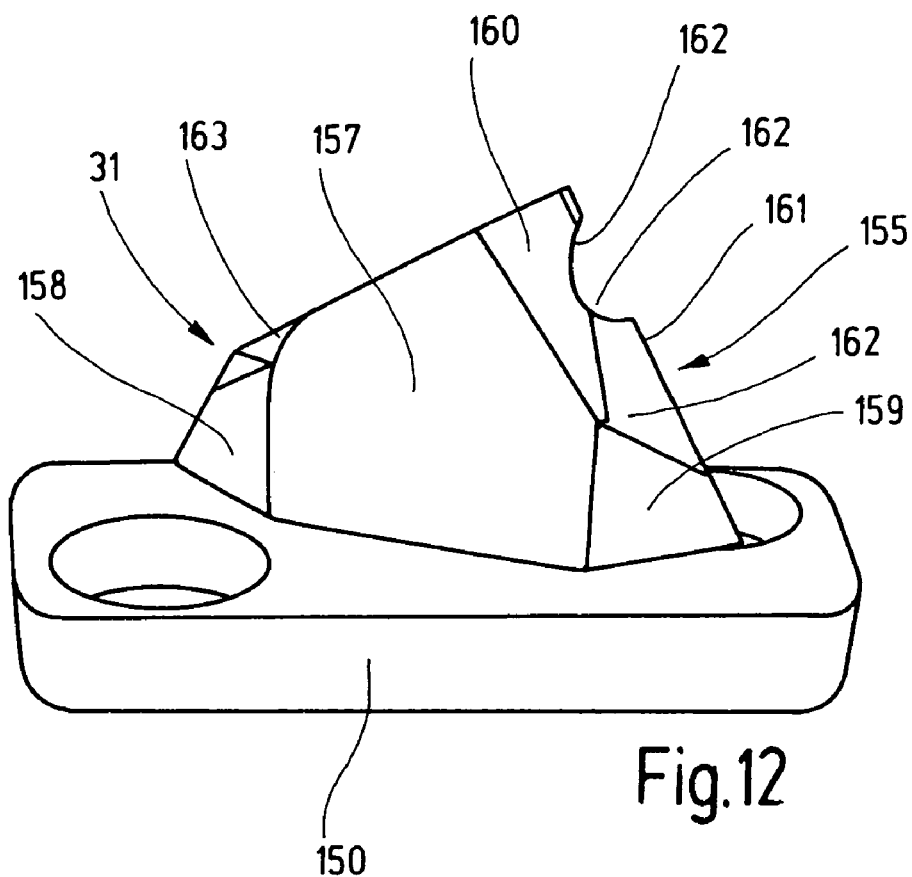
FIG. 12 shows a graphical rear view of the shearing knife.
Figure 13:
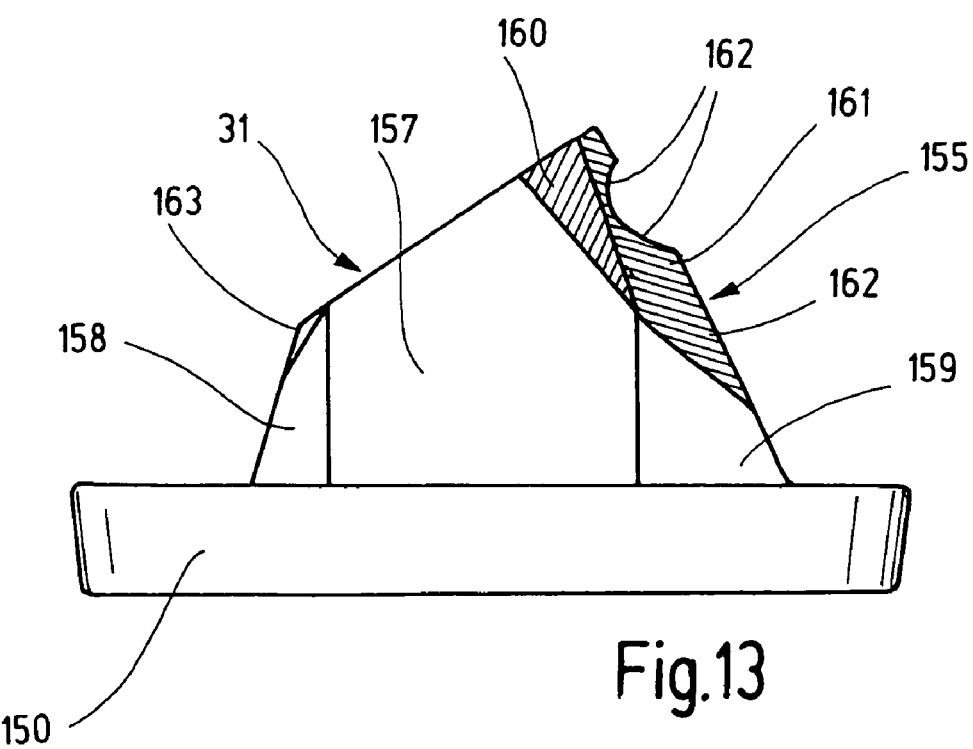
FIG. 13 shows a rear view of the shearing knife.
Figure 14:
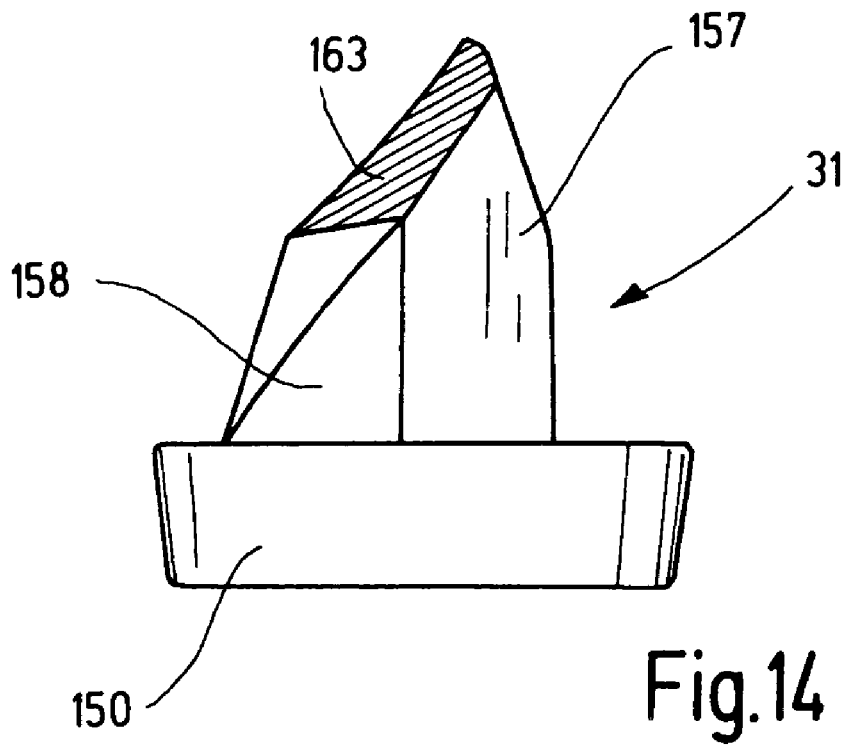
FIG. 14 shows the shearing knife in a view onto its cutting edge.
Figure 15:
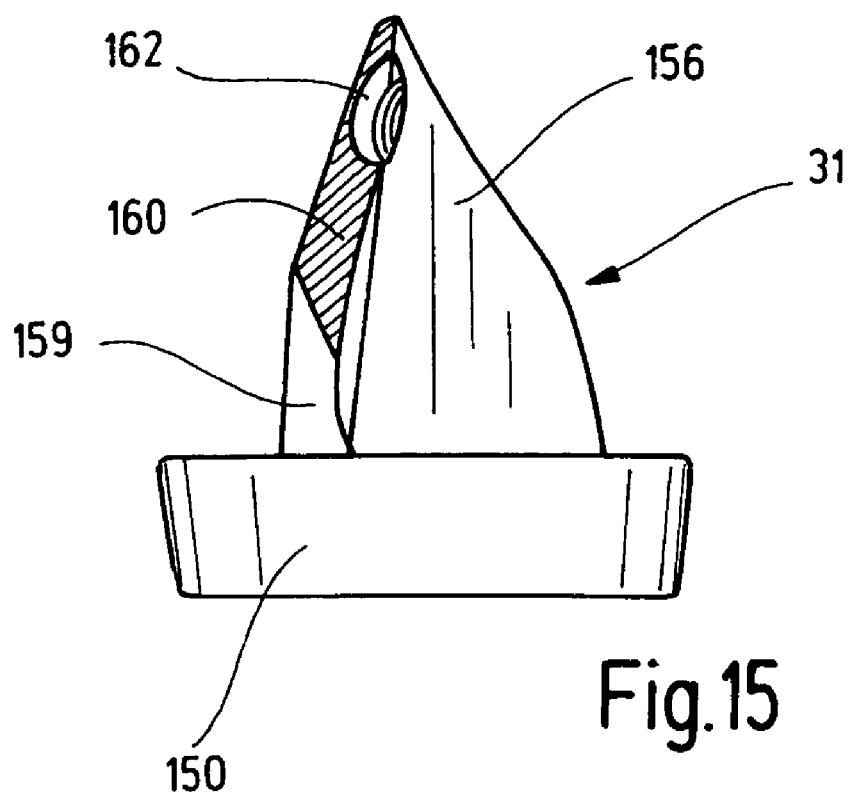
FIG. 15 shows the shearing knife in a view from its cutting and tearing edge.

The one side wall surface 156 of the knife body 155 is curved as an arch to the inside (FIG. 10) while the other side wall surface 157 is plane (FIG. 11). This side wall surface 157 has two side section surfaces 158, 159 which hare U-bent to the side wall surface as well as an upper section surface 160 which is situated in the upper tip area of the knife body 155 which turns into a tapering cutting surface 162 by configuring a cutting edge 161 with a knife-type reduced tearing edge 162 (FIG. 12). The other side edge which extends from the tip area of the knife body 155 to the lateral section surface 158 is configured as cutting edge and cutting surface 163, whereby the reduced tearing edge 162 is configured as a two-sided start ground taper.

Because of the special profile configuration of the knife body 155, a shearing knife 31 is created which has cutting and tearing edges because of the different surface ground sections which make possible an effective comminution of the sanitary waste. The geometrical arrangement of the shearing knives 31 on the knife disk 30 is chosen such that there results an optimal swirl in working and separating direction of the knife disk 31.

The container 20 is provided with an automatically refilling drain trap 50 for aeration (FIG. 2).

The control of the admission for the wash liquid WF and the dosing pumps 28', 29', 129' for the sanitary liquid and for the chemical, the control for the driving device 35 for the knife disk 30 as well as the controls for the discharge device 165, the compressor screw 60 and the pumps are combined in a program switching device or are carried out by means of a free programmable device.

The invention claimed is:

1. A device for the in-situ disposal of sanitary waste, whereby the sanitary waste is mechanically comminuted and at least partially dissolved in a wash liquid, the liquid thus obtained is separated from a remainder of the comminuted sanitary waste, the liquid is supplied to a discharge duct and the remainder of the comminuted sanitary waste is dewatered as well as separately disposed of, the device comprising:

a housing;
a fixed drum-shaped container arranged in the housing and having a horizontal central axis, a filling opening for the sanitary waste, an inlet pipe for dosed wash liquid, an inlet pipe for a dosed sanitary liquid for preventing odors and for disinfection and an inlet pipe for dosed chemicals in powdered or liquid state for conditioning super-absorbers;

a discharge device integrated in a bottom region of the container for carrying-off comminuted sanitary waste interspersed with wash liquid from the bottom region of the container, wherein the discharge device is configured as a conveyor screw, a side wall of the container having a bottom end with a conically downwardly tapered section that opens into the conveyor screw;

a rotatable vertical knife disk arranged in an interior of the container in a region of a side wall of the container, the knife disk having tearing knives directed toward the interior of the container for tearing and disintegrating the sanitary waste;

a compressor screw arranged downstream of the conveyor screw in a substantially tubular housing, The tubular housing and the compressor screw being substantially vertical, the conveyor screw being arranged to exit into a bottom region of the compressor screw, the compressor screw having a different web thickness and different gradient than the conveyor screw;

a switching device for controlling admission of the wash liquid and dosing pumps for the sanitary liquid and for the chemicals;

a drive for rotating the knife disk;

a drive f or the compressor screw and the pumps;

a shear sieve metal sheet arranged within the tubular housing so as to extend in a longitudinal direction of the compressor screw, the compressor screw and the sieve sheet forming a functional unit operative to separate the comminuted sanitary waste containing solid components from the wash liquid with constituents of the sanitary waste dissolved therein, the shear sieve sheet having a curved plate-shape body with a partially circular arch having a radius that corresponds to an outer radius of the compressor screw, the sieve sheet being arranged so that an inner curved surface of the sieve sheet is directly against a peripheral surface of the compressor screw so that the compressor screw and the shear sieve provide a combined shearing action;

a discharge pipe in communication with an interior of the tubular housing;

a pump integrated in the discharge pipe for pumping the wash fluid with the constituents of the sanitary waste dissolved therein to a discharge duct, whereby a remainder of the comminuted sanitary waste freed from liquid and containing solid constituents is fed to a collecting receiver from an upper area of the tubular housing with the compressor screw; and a compressor nozzle with an upwardly tapered section for separating residual liquid from the housing, the nozzle being provided in the upper area of the housing with the compressor screw, the nozzle being connected with the discharge for the liquid from the housing.

2. A device according to claim 1, and further comprising a wash liquid supply operative to supply cold wash liquid to the interior of the container.

3. A device according to claim 1, wherein the container has an upper cylindrical container body which transitions on a bottom side into a tapering section which forms the conveyor screw.

4. A device according to claim 1, wherein the shear sieve sheet is configured as an insert body that is placeable in the tubular housing with the compressor screw.

5. A device according to claim 1, wherein a number of shearing knives placed distributed over the disk surface is provided on a wall surface of the knife disk that faces the interior of the container.

6. A device according to claim 1, wherein the container has a length that substantially corresponds to a diameter of front walls of the drum-shaped container, the knife disk having a diameter that substantially corresponds to a diameter of the front walls in an area above the conveyor screw.

7. A device according to claim 1, wherein the container is supported elastically in a frame of the housing.

8. A device according to claim 1, wherein each shearing knife has an optimized knife grinding for an effective comminution of the sanitary waste and is made of a substantially rectangular fixing plate and a plate-shaped and substantially triangular knife body placed upright on the fixing plate and diagonally to the fixing plate, one side wall surface of the knife body being curved inwardly as an arch while the other side wall surface is planar and has two side sections which are bent to the other side wall surface as well as a bent upper section surface which is situated in an upper tip area of the knife body which turns into a tapering cutting surface by forming a cutting edge with a reduced tearing edge, whereby another side edge which extends from the tip area of the knife body to a lateral section surface is configured as a cutting edge and cutting surface, whereby the reduced tearing edge is configured as a two-sided polished taper.

9. A device according to claim 1, wherein the container is provided with an automatically refilling drain trap for aeration.

* * * * *